United States Patent
Bohn et al.

(10) Patent No.: US 8,227,490 B2
(45) Date of Patent: *Jul. 24, 2012

(54) USE OF 1-HYDROXY-2-PYRIDONES FOR THE TREATMENT OF SEBORRHEIC DERMATITIS

(75) Inventors: Manfred Bohn, Hofheim (DE); Karl Theodor Kraemer, Langen (DE); Astrid Markus, Liederbach (DE)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,710

(22) Filed: Jul. 7, 2011

(65) Prior Publication Data

US 2011/0269801 A1    Nov. 3, 2011

Related U.S. Application Data

(60) Continuation of application No. 13/018,417, filed on Jan. 31, 2011, now Pat. No. 7,981,909, which is a continuation of application No. 12/563,774, filed on Sep. 21, 2009, now abandoned, which is a continuation of application No. 10/606,229, filed on Jun. 26, 2003, now abandoned, which is a division of application No. 09/077,194, filed as application No. PCT/EP97/05070 on Sep. 16, 1997, now abandoned.

(30) Foreign Application Priority Data

Sep. 27, 1996   (DE) .................................. 196 39 818

(51) Int. Cl.
- *A01N 43/40*     (2006.01)
- *A61K 31/44*     (2006.01)
- *C07D 211/72*    (2006.01)
- *C07D 211/84*    (2006.01)

(52) U.S. Cl. ........ 514/345; 514/277; 514/352; 514/852; 514/861; 514/863; 514/864; 514/881; 546/290; 546/294; 546/295; 546/300; 546/301; 546/302

(58) Field of Classification Search .................. 514/345, 514/277, 352, 852, 861, 863, 864, 881; 516/290, 516/294, 295, 300, 301, 302; 546/290, 294, 546/295, 300, 301, 302
See application file for complete search history.

(56) References Cited

U.S. PATENT DOCUMENTS

| | | | | |
|---|---|---|---|---|
| 4,185,106 A | * | 1/1980 | Dittmar et al. | ............... 514/336 |
| 6,075,017 A | * | 6/2000 | Dascalu et al. | ............... 514/188 |

FOREIGN PATENT DOCUMENTS

| | | | |
|---|---|---|---|
| EP | 0771187 | * | 5/1997 |
| GB | 2180846 | * | 4/1987 |
| WO | WO 96/02226 | * | 2/1996 |

OTHER PUBLICATIONS

Hanel, H. "Treatment of Seborrheic Eczema Using an Antimycotic with Antiphogistic Properties," Mycoses, 1991,34, Suppl. 1, p. 91-93).*

* cited by examiner

*Primary Examiner* — Michael G Hartley
*Assistant Examiner* — Leah Schlientz
(74) *Attorney, Agent, or Firm* — William J. McNichol, Jr.; Maryellen Feehery Hank; Reed Smith LLP

(57) ABSTRACT

Compounds of the formula (I) are disclosed and are suitable for the treatment of seborrheic dermatitis.

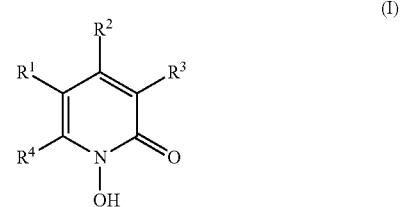

(I)

1 Claim, No Drawings

USE OF 1-HYDROXY-2-PYRIDONES FOR THE TREATMENT OF SEBORRHEIC DERMATITIS

RELATED APPLICATIONS

This application is a continuation application of U.S. application Ser. No. 13/018,417 (now U.S. Pat. No. 7,981,909), filed Jan. 31, 2011, which is a continuation of U.S. application Ser. No. 12/563,774, filed Sep. 21, 2009 (now abandoned), which is a continuation of U.S. application Ser. No. 10/606,229, filed Jun. 26, 2003 (now abandoned), which is a divisional of U.S. application Ser. No. 09/077,194, filed Dec. 4, 1998 (now abandoned), which is a U.S. National Stage of International Application No. PCT/EP97/05070 filed Sep. 16, 1997, which are herein incorporated by reference.

Seborrheic dermatitis is understood as meaning a disorder of the scalp which differs from simple dandruff by the presence of erythema as a sign of inflammation, by the greater degree of scaling with occasional itching and burning, and by the occurrence of eczematous changes to other body sites. It can occur in the form of patches, but also more frequently affects the whole scalp and often includes, beyond the hairline, the forehead, around the neck and the ears. In severe cases, the scalp can have a secondary infection, and the changes can then exhibit a spongy consistency, vesicle and crust formation and can weep.

Seborrheic dermatitis frequently occurs even in infancy and usually remits spontaneously at an age of 8-12 months. The scalp changes consisting of erythema, scaling and occasionally vesicles and crusts in infants can regress spontaneously within a few weeks, intermittently reoccur or persist during the entire childhood. They are frequently combined with a similar process around the eyelids, nose and ears. Later, the condition usually occurs after puberty and can last for the whole life or even increase in strength. Approximately 1-3% of the population are affected by this illness.

It is known that 1-hydroxy-2-pyridones and their salts exhibit activity against normal dandruff which is characterized by a clinically noninflammatory scaling of the scalp occurring in nearly all people (DE 22 34 009).

The most promising type of treatment of seborrheic dermatitis until now was the topical application of corticosteroid preparations, but more recently topical therapy with antimycotic substances has gained, importance.

While corticosteroid preparations display their activity exclusively via an effect on the inflammatory process, the antimycotic substances such as ketoconazole are active exclusively against the yeast fungi of the strain Pityrosporum which is assumed to be the cause of seborrheic dermatitis. The 1-hydroxy-2-pyridones according to the invention, however, combine the properties of both classes of substance in one substance and exhibit both anti-inflammatory action and antimycotic activity against Pityrosporum strains.

In comparison to ketoconazole, the substances according to the invention—even after only a short topical contact time—concentrate rapidly in the skin layers which are relevant for fungal growth and thus contribute to a rapid cure.

While, ketoconazole is inactive in vitro against gram-positive bacteria (Kinsman et al., J. Med. Microbiol. (1983) 16, No. 2, IV), the hydroxy-pyridones according to the invention exhibit activity against gram-positive and gram-negative aerobic, and anaerobic bacteria (Dittmar et al., Arzneim.-Forschung, (1981) 31 (II), No. 8a, pp. 1317-1322): With respect to the treatment of secondarily infected cases, this is an extremely important finding.

Compared with ketoconazole, the compounds used according to the invention furthermore have very crucial advantages with respect to their processing possibilities in pharmaceutical preparations. On account of their solubility in water, alcohols and aqueous-alcoholic solutions, the preparation of hair lotions and transparent gel preparations is possible without problems.

The preparations according to the invention can also be employed for the treatment of Pityriasis versicolor, a superficial, noninflammatory skin fungus disorder on the trunk.

The invention therefore relates to the use of 1-hydroxy-2-pyridones of the formula I

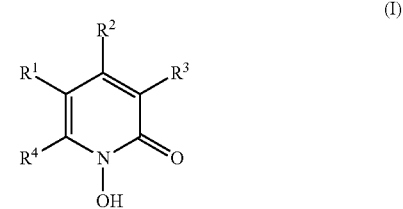

in which $R^1$, $R^2$ and $R^3$, which are identical or different, are a hydrogen atom or alkyl having 1-4 carbon atoms, and $R^4$ is a saturated hydrocarbon radical having 6 to 9 carbon atoms or a radical of the formula II

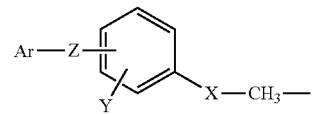

where
X is S or O,
Y is a hydrogen atom or up to 2 halogen atoms such as chlorine and/or bromine,
Z is a single bond or the bivalent radicals O, S, —$CR^2$— (R=H or ($C_1$-$C_4$)-alkyl) or other bivalent radicals having 2-10 carbon and, if appropriate, oxygen and/or sulfur atoms linked in the form of a chain, where—if the radicals contain 2 or more oxygen and/or sulfur atoms—the latter must be separated from one another by at least 2 carbon atoms and where 2 adjacent carbon atoms can also be linked to one another by a double bond and the free valences of the carbon atoms are saturated by H and/or ($C_1$-$C_4$)-alkyl groups,
Ar is an aromatic ring system having up to two rings which can be substituted by up to three radicals from the group consisting of fluorine, chlorine, bromine; methoxy, ($C_1$-$C_4$)-alkyl, trifluoromethyl and trifluoromethoxy, in free or in salt form,
for the production of a pharmaceutical for the treatment of seborrheic dermatitis.

In the radicals "Z", the carbon chain members are preferably $CH_2$ groups. If the $CH_2$ groups are substituted by $C_1$-$C_4$-alkyl groups, $CH_3$ and $C_2H_5$ are preferred substituents. Exemplary radicals "Z" are:

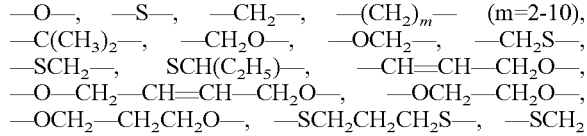

$-CH_2CH_2CH_2O-$, $-SCH_2CH_2OCH_2CH_2O-$, $-SCH_2CH_2OCH_2CH_2O-CH_2CH_2S-$ or $-S-CH_2-C(CH_3)_2-CH_2-S-$.

The radical "S" is a sulfur atom, the radical "O" is an oxygen atom. The term "Ar" denotes phenyl or fused systems such as naphthyl, tetrahydronaphthyl and indenyl, and also isolated systems as such, which are derived from biphenyl, diphenylalkanes, diphenyl ethers and diphenyl thioethers.

In the formula I, the hydrocarbon radical $R^4$ is an alkyl or cyclohexyl radical which can also be bonded to the pyridone ring via a methylene or ethylene group or can contain an endomethyl group. $R^4$ can also be an aromatic radical which, however, is preferably bonded to the pyridone radical via at least one aliphatic carbon atom:

Important representatives of the class of compounds characterized by the formula I are:

6-[4-(4-chlorophenoxy)phenoxymethyl]-1-hydroxy-4-methyl-2-pyridone, 6-[4-(2,4-dichlorophenoxy)phenoxymethyl]-1-hydroxy-4-methyl-2-pyridone, 6-(biphenyl-4-oxymethyl)-1-hydroxy-4-methyl-2-pyridone, 6-(4-benzylphenoxymethyl)-1-hydroxy-4-methyl-2-pyridone, 6-(4-(2,4-dichlorobenzyloxy)phenoxymethyl)-1-hydroxy-4-methyl-2-pyridone, 6-[4-(4-chlorophenoxy)phenoxymethyl]-1-hydroxy-3,4-dimethyl-2-pyridone, 6-[4-(2,4-dichlorobenzyl)phenoxymethyl]-1-hydroxy-3,4-dimethyl-2-pyridone, 6-[4-cinnamyloxy)phenoxymethyl]-1-hydroxy-4-methyl-2-pyridone, 1-hydroxy-4-methyl-6-[4-(4-trifluoromethylphenoxy)phenoxymethyl]-2-pyridone, 1-hydroxy-4-methyl-6-cyclohexyl-2-pyridone, 1-hydroxy-4-methyl-6-(2,4,4-trimethylpentyl)-2-pyridone, 1-hydroxy-4-methyl-6-n-hexyl-, -6-isohexyl-, -6-n-heptyl- or -6-isoheptyl-2-pyridone, 1-hydroxy-4-methyl-6-octyl- or -6-isooctyl-2-pyridone, in particular 1-hydroxy-4-methyl-6-cyclohexyl methyl- or -6-cyclohexylethyl-2-pyridone, where the cyclohexyl radical can in each case also carry a methyl radical, 1-hydroxy-4-methyl-6-(2-bicyclo[2,2,1]heptyl)-2-pyridone, 1-hydroxy-3,4-dimethyl-6-benzyl- or -6-dimethylbenzyl-2-pyridone or 1-hydroxy-4-methyl-6-(β-phenylethyl)-2-pyridone.

The term "saturated" in this case designates those radicals which contain no aliphatic multiple bonds, i.e. no ethylenic or acetylenic bonds.

The abovementioned compounds of the formula I can be employed either in free form or as salts, use in free form is preferred.

If organic bases are used, poorly volatile bases are preferably employed, for example low molecular weight alkanolamines such as ethanolamine, diethanolamine, N-ethylethanolamine, N-methyldiethanolamine, triethanolamine, diethylaminoethanol, 2-amino-2-methyl-n-propanol, dimethylaminopropanol, 2-amino-2-methylpropanediol, triisopropanolamine. Further poorly volatile bases which may be mentioned are, for example, ethylenediamine, hexamethylenediamine, morpholine, piperidine, piperazine, cyclohexylamine, tributylamine; dodecylamine, N,N-dimethyldodecylamine, stearylamine, oleylamine, benzylamine, dibenzylamine, N-ethylbenzylamine, dimethylstearylamine, N-methylmorpholine, N-methylpiperazine, 4-methylcyclohexylamine, N-hydroxyethylmorpholine. The salts of quaternary ammonium hydroxides such as trimethylbenzylammonium hydroxide, tetramethylammonium hydroxide or tetraethylammonium hydroxide can also be used, furthermore guanidine and its derivatives, in particular its alkylation products. However, it is also possible to employ as salt-forming agents, for example, low molecular weight alkylamines such as methylamine, ethylamine or triethylamine. Suitable salts for the compounds to be employed according to the invention are also those with inorganic cations, for example alkali metal salts, in particular sodium, potassium or ammonium salts, alkaline earth metal salts such as, in particular, the magnesium or calcium salts, as well as salts with bi- or tetravalent cations, for example the zinc, aluminum or zirconium salt.

The active compounds to be employed in the preparations of the compound of the formula I can be prepared, for example, according to processes given in U.S. Pat. No. 2,540,218.

For the use according to the invention of the compounds mentioned, liquid to semisolid pharmaceutical preparations, in particular hair lotions, shampoos, liquid soaps, as well as cream, ointment and gel preparations, are suitable.

In this case, these are always preparations which, depending on their actual intended use, are applied to the skin and/or to the scalp for a shorter or longer time. Due to the addition of the compounds according to the invention, an effective treatment of the seborrheic dermatitis is brought about.

If the preparations according to the invention are present as shampoo, they can be in clear liquid or opaque liquid form, in cream form or even gelatinous. The surfactants on which these shampoos are based can be of anionic, cationic, non-ionic or amphoteric nature and can-also be present as a combination of these substances.

Preferably, however, anionic surfactants are employed on their own or as a mixture with other anionic surfactants as base surfactants—if appropriate with addition of amphoteric surfactants as cosurfactant.

As the sole detergent substances, amphoteric surfactants are virtually insignificant, since their foaming behavior, thickenability and partly also skin and eye mucous membrane tolerability are only moderate. In combination with various anionic surfactants, however, precisely these properties are synergistically improved. This explains the relatively great importance of the amphoteric surfactants for the optimization of anionic shampoo bases.

Nonionic surfactants can also be employed as cosurfactants.

Examples of anionic detergent substances of this type which may be mentioned are: ($C_{10}$-$C_{20}$)-alkyl- and -alkylenecarboxylates, alkyl ether carboxylates, fatty alcohol sulfates, fatty alcohol ether sulfates, alkylolamide sulfates and sulfonates, fatty acid alkylamide polyglycol ether sulfates, alkanesulfonates and hydroxyalkanesulfonates, olefinsulfonates, acyl esters of isothionates, α-sulfofatty acid esters, alkylbenzosulfonates, alkylphenol glycol ether sulfonates, sulfosuccinates, sulfosuccinic acid hemiesters and diesters, fatty alcohol ether phosphates, protein-fatty acid condensation products, alkylmonoglyceride sulfates and sulfonates, alkylglyceride ether sulfonates, fatty acid methyltaurides, fatty acid sarcosinates or sulforicinoleates. These compounds and their mixtures are used in the form of their water-soluble or water-dispersible salts, for example the sodium, potassium, magnesium, ammonium, mono-, di- and triethanolammonium as well as analogous alkylolammonium salts.

Examples of amphoteric surfactants which can be added to the shampoos are: N—(($C_{12}$-$C_{18}$)-alkyl)-β-aminopropionates and N—(($C_{12}$-$C_{18}$)-alkyl) β-iminodipropionates as alkali metal and mono-, di- and trialkylolammonium salts; N-acylamidoalkyl-N,N-dimethylacetobetaine, preferably N—(($C_8$-$C_{18}$)-acyl)amidopropyl-N,N-dimethylacetobetaine; ($C_{12}$-$C_{18}$)-alkyldimethylsulfopropylbetaine; amphoteric surfactants based on imidazoline (trade name; Miranol®, Steinapon®), preferably the sodium salt of 1-(β-carboxymethyloxyethyl)-1-(carboxymethyl)-2-laurylimidazolinium;

amine oxides, e.g. $(C_{12}-C_{18})$-alkyldimethylamine oxide or fatty acid amidoalkyldimethylamine oxide.

Suitable nonionic surfactants which can be employed as detergent substances are, for example: fatty alcohol ethoxylates (alkyl polyethylene glycols); alkylphenol polyethylene glycols; alkylmercaptan polyethylene glycols; fatty amine ethoxylates (alkylamino polyethylene glycols); fatty acid ethoxylates (acyl polyethylene glycols), polypropylene glycol ethoxylates (Pluronic®); fatty acid alkylolamides (fatty acid amide polyethylene glycols); sucrose esters; alkyl polyglucosides; sorbitol esters and polyglycol ether.

Suitable cationic surfactants are, for example; quaternary ammonium salts such as di-(($C_{10}-C_{24}$)-alkyl)dimethylammonium chloride or bromide, preferably di-(($C_{12}-C_{18}$)-alkyl) dimethylammonium chloride or bromide; ($C_{10}-C_{24}$)-alkyldimethylethylammonium chloride or bromide; ($C_{10}-C_{24}$)-alkyltrimethylammonium chloride or bromide, preferably cetyltrimethylammonium chloride or bromide and ($C_{20}-C_{22}$)-alkyltrimethylammonium chloride or bromide; ($C_{10}-C_{24}$)-alkyldimethylbenzylammonium chloride or bromide; preferably ($C_{12}-C_{18}$)-alkyldimethylbenzylammonium chloride; N—(($C_{10}-C_{18}$)-alkyl)pyridinium chloride or bromide, preferably N—(($C_{12}-C_{16}$) alkyl)pyridinium chloride or bromide; N—(($C_{10}-C_{18}$)-alkyl)isoquinolinium chloride, bromide or monoalkylsulfate; N—(($C_{12}-C_{18}$)-alkylolaminoformylmethyl)pyridinium chloride; N—(($C_{12}-C_{18}$)-alkyl)-N-methylmorpholinium chloride, bromide or monoalkylsulfate, N—(($C_{12}-C_{18}$)-alkyl)-N-methylmorpholinium chloride, bromide or monoalkylsulfate; ($C_{16}-C_{18}$) alkylpentaoxethylammonium chloride; diisobutylphenoxyethoxyethyl-dimethylbenzylammonium chloride; salts of N,N-diethylaminoethylstearylamide and -oleylamide with hydrochloric acid, acetic acid, lactic acid, citric acid, phosphoric acid; N-acylamidoethyl-N,N-diethyl-N-methylammonium chloride, bromide or monoalkylsulfate and N-acylamidoethyl-N,N-diethyl-N-benzylammonium chloride, bromide or monoalkylsulfate, where acyl is preferably stearyl or oleyl.

The preparations according to the invention can additionally contain further additives, e.g. aromatic substances, colorants, opacifiers and pearl luster agents, for example esters of fatty acids and polyols, magnesium and zinc salts of fatty acids, dispersions based on copolymers, thickeners such as sodium, potassium or ammonium chloride, sodium sulfate, fatty acid alkylolamides, cellulose derivatives of natural gums, collagen hydrolyzates, furthermore fats, oils, fatty alcohols, silicones, substances having a keratolytic and keratoplastic action, for example sulfur, salicylic acid or enzymes.

The shampoos are prepared in a manner known per se by mixing together of the individual components and a further processing—if necessary—suited to the particular type of preparation. Some of these various possible preparations are described by way of example in the working examples.

The preparations according to the invention can also be present in the form of aqueous and aqueous-alcoholic hair lotions, and also those in gel form and in aerosol form as spray or foam. Alcohols employed are preferably ethanol and isopropyl alcohol.

Further preparations which may be mentioned in which the 1-hydroxy-2-pyridones can be used according to the invention are, for example, cream and ointment preparations, products which are primarily used for the treatment of hairless head and body parts.

The preparation of all these preparations is also carried out—as already mentioned in the case of shampoo—in a manner known per se with addition of the active compound employed according to the invention. Of the abovementioned 1-hydroxy-2-pyridones, the preparations according to the invention can contain one compound or even several in combination.

The pH of the preparations is in the skin-physiological range of approximately pH 4.5 to 6.5. Whereas, when using the compounds in salt form, the adjustment of the pH range mentioned has to be carried out using organic acids, this measure is not necessary when using the free compounds.

In the preparations according to the invention, the active compounds is incorporated in amounts which are customarily between approximately 0.05 and approximately 10%. Within this range, the concentrations of the specific preparations depend on their intended use. Certain preparation forms such as concentrates, which are to be diluted before use, can have considerably higher concentrations.

If they are preparations which remain on the skin and on the scalp, for example gel preparations, ointments, creams or hair lotions, lower concentrations will be employed, for example from about 0.05% to about, 1%, preferably from 0.1 to 0.5%. In higher concentrations, they will expediently be used when they are preparations which, optionally after dilution, only act on the scalp for a short time, for example shampoos or liquid soaps. In these cases, for example, concentrations of approximately 0.2 to approximately 10%, preferably from approximately 0.5% to approximately 2%, can be expedient.

The following quantitative data relate to the weight, if not stated otherwise.

EXAMPLE 1

A preparation according to the invention has the following composition:

| Shampoo (based on anionic detergent substances) | |
|---|---|
| 1-Hydroxy-4-methyl-6-cyclohexyl-2(1H)pyridone | 1.00% |
| Sodium lauryl diglycol ether sulfate (27% strength solution) | 40.00% |
| Disodium lauryl polyglycol ethersulfosuccinate (33% strength solution) | 10.00% |
| Sodium chloride | 2.50% |
| Water | 46.50% |

EXAMPLE 2

A preparation according to the invention has the following composition:

| Shampoo (based on anionic detergent substance with amphoteric surfactant as cosurfactant) | |
|---|---|
| 1-Hydroxy-4-methyl-6-cyclohexyl-2(1H)pyridone | 1.00% |
| Sodium lauryl diglycol ether sulfate (27% strength solution) | 36.00% |
| Cocamidopropylbetaine (30% strength solution) | 6.00% |
| Sodium chloride | 3.30% |
| Water | 53.70% |

EXAMPLE 3

A preparation according to the invention has the following composition:

| Shampoo (based on anionic detergent substance with nonionic surfactant as cosurfactant) | |
| --- | --- |
| 1-Hydroxy-4-methyl-6-cyclohexyl-2(1H)pyridone | 1.50% |
| Sodium lauryl diglycol ether sulfate (27% strength solution) | 30.00% |
| Lauryl alcohol polyglucoside | 8.00% |
| Sodium chloride | 2.00% |
| Water | 58.50% |

EXAMPLE 4

A preparation according to the invention has the following composition:

| Liquid soap | |
| --- | --- |
| 1-Hydroxy-4-methyl-6-cyclohexyl-2(1H)pyridone | 1.00% |
| Sodium lauryl diglycol ether sulfate (27% strength solution) | 35.00% |
| Cocamidopolyglycol ether sulfate magnesium salt (30% strength solution) | 8.00% |
| Cocamidopropylbetaine (30% strength solution) | 10.00%0 |
| Lauryl alcohol glycol ether | 2.00% |
| Sodium chloride | 2.00% |
| Water | 42.00% |

EXAMPLE 5

A preparation according to the invention has the following composition:

| Hair lotion | |
| --- | --- |
| 1-Hydroxy-4-methyl-6-[4-(4-chlorophenoxy)phenoxymethyl] 2(1H)pyridone | 0.05% |
| 2-Propanol | 60.00% |
| Water | 39.95% |

EXAMPLE 6

A preparation according to the invention has the following composition:

| Gel preparation | |
| --- | --- |
| 1-Hydroxy-4-methyl-6-cyclohexyl-2(1H)pyridone | 0.75% |
| 2-Propanol | 15.00% |
| 2-Octyldodecanol | 7.5% |

| Gel preparation | |
| --- | --- |
| Carbomer 4,000,000 | 0.50% |
| Polysorbate 60 | 1.50% |
| Sodium hydroxide | 0.18% |
| Water | 74.57% |

EXAMPLE 7

A preparation according to the invention has the following composition:

| Cream preparation | |
| --- | --- |
| 1-Hydroxy-4-methyl-6-cyclohexyl-2(1H)-pyridone, aminoethanol salt 1:1 | 1.00% |
| 2-Octyldodecanol | 7.5% |
| Liquid paraffin | 7.50% |
| Stearyl alcohol | 7.50% |
| Cetyl alcohol | 7.50% |
| Polysorbate 60 | 3.00% |
| Sorbitan monostearate | 2.00% |
| Lactic acid, 90% strength | 0.51% |
| Water | 63.49% |

EXAMPLE 8

In a clinical study with a total of 180 patients, it was possible to show that the symptoms of seborrheic dermatitis of the scalp (severe scaling, inflammation, itching) can be effectively treated by a 1-2× weekly treatment with a 1% strength ciclopirox shampoo preparation over a period of 4 weeks.

EXAMPLE 9

In a clinical study, it was possible to successfully treat 180 patients with seborrheic dermatitis of the scalp, of the face and of the upper body by application of a 0.77% strength ciclopirox gel preparation over a period of 4 weeks.

The invention claimed is:
1. A method of treating seborrheic dermatitis comprising administering to the affected area of the skin of a human having seborrheic dermatitis an amount effective for the treatment of seborrheic dermatitis of a composition comprising only one active ingredient, the active ingredient consisting of ciclopirox, and at least one surfactant; wherein the composition has a pH ranging from about 4.5 to about 6.5; and wherein the composition is a single composition.

* * * * *